United States Patent [19]
Oppong et al.

[11] Patent Number: 5,494,904
[45] Date of Patent: Feb. 27, 1996

[54] SYNERGISTIC ANTIMICROBIAL COMPOSITIONS CONTAINING 2-(THIOCYANOMETHYLTHIO)BENZO-THIAZOLE AND AN ORGANIC ACID

[75] Inventors: David Oppong, Memphis; C. George Hollis, Germantown, both of Tenn.

[73] Assignee: Buckman Laboratories International, Inc., Memphis, Tenn.

[21] Appl. No.: 125,849

[22] Filed: Sep. 24, 1993

[51] Int. Cl.$^6$ .......................... A01N 37/10; A01N 37/36; A01N 43/00; A01N 43/78

[52] U.S. Cl. .......................... 514/161; 514/159; 514/367; 514/568

[58] Field of Search .................................. 514/159, 161, 514/367, 568

[56] References Cited

U.S. PATENT DOCUMENTS

| | | | |
|---|---|---|---|
| 3,231,509 | 1/1966 | Shema | 252/177 |
| 3,520,976 | 7/1970 | Buckman et al. | 424/270 |
| 4,303,668 | 12/1981 | Hasegawa et al. | 424/279 |
| 4,479,961 | 10/1984 | Martin | 424/270 |

FOREIGN PATENT DOCUMENTS

| | | |
|---|---|---|
| 1207952 | 7/1986 | Canada . |
| 62-165723 | 3/1987 | Japan . |
| 63-094512 | 2/1988 | Japan . |
| 4-320743 | 8/1992 | Japan . |
| 94206391 | 11/1992 | Japan . |
| WO92/19104 | 11/1992 | WIPO . |
| WO92/21239 | 12/1992 | WIPO . |

OTHER PUBLICATIONS

Kull, et al., Mixtures of Quaternary Ammonium Compounds and Long Chain Fatty Acids as Antifungal Agents, 1961. Applied Microbiology, 9: 538–541.

Chemical Abstracts, vol. 119, No. 5, Abstract No. 43363, Aug. 2, 1993 Kamlmoto et al.

Chemical Abstracts, vol. 117, No. 13, Abstract No. 126464, Sep. 28, 1992.

The Merck Index, 10th ed (1983) pp. 155, 156, 200+1200.

*Primary Examiner*—Allen J. Robinson
*Attorney, Agent, or Firm*—Finnegan, Henderson, Farabow, Garrett, & Dunner

[57] ABSTRACT

Compositions comprising 2-(thiocyanomethylthio)benzothiazole and at least one organic acid or its salt are disclosed which are synergistically effective compared to the respective components alone in controlling the growth of microorganisms in or on a material or medium. Methods to control the growth of microorganisms and prevent spoilage caused by microorganisms with the use of the compositions of the present invention are also disclosed.

24 Claims, No Drawings

SYNERGISTIC ANTIMICROBIAL COMPOSITIONS CONTAINING 2-(THIOCYANOMETHYLTHIO)BENZO-THIAZOLE AND AN ORGANIC ACID

The present invention relates to certain compositions and processes useful for controlling the growth of one or more microorganisms and for preventing spoilage caused by bacteria and fungi in various products, materials, or media, particularly industrial products, materials or media. These materials or media include wood pulp, wood chips, lumber, adhesives, coatings, animal hides, paper mill liquors, pharmaceutical formulations, cosmetics and toiletry formulations, geological drilling lubricants, agrochemical compositions, paints, leathers, wood, metalworking fluids, cooling tower water, tanning liquors, starch, petrochemicals, proteinaceous materials, acrylic latex paint emulsions, and textiles. The novel processes and mixtures of the present invention show unexpected synergistic activity against microorganisms, including bacteria and fungi. Specifically, the invention is directed to the use of compositions comprising 2-(thiocyanomethylthio)benzothiazole and at least one organic acid or salt thereof.

Many of the products, materials, or media referred to above, when wet or subjected to treatment in water, are susceptible to bacterial and/or fungal deterioration or degradation unless steps are taken to inhibit such degradation or deterioration.

To control deterioration or degradation caused by microorganisms, various industrial microbicides are used. Workers in the trade have continued to seek improved biocides that have low toxicity and are capable of exhibiting a prolonged biocidal Organic acids can be used alone to control microorganisms, but many of them have low efficacy against bacteria and fungi unless extremely high concentrations are used. 2-(Thiocyanomethylthio)benzothiazole (TCMTB) can also be used alone in low concentrations as a biocide.

It is an object of this invention to provide a microbicidal composition capable of controlling the growth of at least one microorganism, particularly fungi and bacteria, over prolonged periods of time. It is an additional object to provide such compositions which are economical to use. Methods of controlling the growth of at least one microorganism are also objects of this invention.

The present invention provides a composition comprising 2-(thiocyanomethylthio)-benzothiazole and at least one organic acid or its salt, where the components are present in a combined amount synergistically effective to control the growth of at least one microorganism.

The present invention also provides a method for controlling the growth of at least one microorganism in or on a material or medium susceptible to attack by the microorganism which comprises the step of adding to the material or medium a composition of the present invention in an amount synergistically effective to control the growth of the microorganism. The synergistically effective amount varies in accordance with the material or medium to be treated and can, for a particular application, be routinely determined by one skilled in the art.

The present invention also embodies the separate addition of 2-(thiocyanomethylthio)benzothiazole and at least one organic acid or its salt to the products, materials or media described above. According to this embodiment, the components are individually added to the system so that the final amount of 2-(thiocyanomethylthio)benzothiazole and at least one organic acid or its salt present in the system at the time of use is that amount synergistically effective to control the growth of at least one microorganism.

The compositions of the present invention are also useful in preserving various types of industrial media or materials susceptible to attack by microorganisms. Such media or materials include but are not limited to dyes, pastes, lumber, leather, textiles, pulp, wood chips, tanning liquors, paper mill liquors, polymer emulsions, paints, metalworking fluids, geological drilling lubricants, cooling water systems, pharmaceutical formulations, cosmetics and toiletry formulations.

The composition can also be useful in agrochemical formulations for the purpose of protecting seeds or crops against microbial spoilage.

Additional objects and advantages of the present invention will be set forth in part in the description which follows, and in part will be obvious from the description, or may be learned by the practice of the present invention. The objects and advantages of the present invention may be realized and obtained by means of the elements and combinations particularly pointed out in the claims.

It is to be understood that both the foregoing general description and the following general description are exemplary and explanatory only and are not restrictive of the present invention as claimed.

When two chemical microbicides are combined into one product or added separately three results are possible:

1) The resulting product would produce an additive (neutral) effect.

2) The products in the product would produce an antagonistic effect, or

3) The chemicals in the product would produce a synergistic effect.

An additive effect has no economic advantage over the individual components. The antagonistic effect would produce a negative impact. Only a synergistic effect, which is less likely than either an additive or antagonistic effect, would produce a positive effect and therefore possess economic advantages.

The microbicidal compositions combining 2-(thiocyanomethylthio)benzothiazole and at least one organic acid or its salt demonstrate an unexpected synergistic effect compared to the respective components alone. Thus, these compositions achieve superior, i.e. greater than additive, microbicidal activity at low concentrations against a wide variety of microorganisms. Examples of microorganisms include fungi and bacteria such as *Trichoderma viride* and *Pseudomonas aeruginosa*. Preferably, the compositions of the present invention have a low toxicity.

The preparation of 2-(thiocyanomethylthio)benzothiazole (TCMTB) is described in U.S. Pat. No. 3,520,976. TCMTB is commercially available and also easily synthesized from commercially available raw materials.

The organic acid can be any organic acid that will produce a synergistic effect when combined with 2-(thiocyanomethylthio)benzothiazole. Examples include aromatic organic acids, cyclic organic acids, aliphatic organic acids or their salts. Specific examples of effective organic acids include dehydroacetic acid, octanoic acid, nonanoic acid, formic acid, sorbic acid, acetic acid, oxalic acid, glycolic acid, citric acid, gluconic acid, malic acid, propionic acid, lauric acid, undecylenic acid, benzoic acid or derivatives of benzoic acid such as 2-hydroxybenzoic acid, 3-hydroxybenzoic acid or 4-hydroxybenzoic acid. The salts of the organic acids, particularly those containing calcium, zinc, potassium, or sodium may also be used. Further, mixtures of organic acids can also be used. When such mixtures are used in combination with TCMTB, at least one of the organic acids in the mixtures has a synergistic relationship with the TCMTB. Organic acids useful in the invention are commercially available or may be synthesized from commercially available raw materials.

The organic acid may be chosen based on the compatibility with the materials or media. Compatibility is determined by criteria such as solubility in the fluid system and lack of reactivity with the fluid, material, or media in question. The compatibility is readily determined by one having ordinary skill in the art by adding the organic acid to the material or media to be used. When used in a fluid system it is preferable that the organic acid be freely soluble in the particular fluid resulting in a uniform solution or dispersion.

In the following discussion of preferred embodiments, component (a) is 2-(thiocyanomethylthio)benzothiazole and component (b) is an organic acid or its salt.

As described above, components (a) and (b) are used in synergistically effective amounts. The weight ratios of (a) to (b) vary depending on the type of microorganisms, material, or media to which the composition is applied. One skilled in the art can readily determine without undue experimentation, the appropriate weight ratios for a specific application. Generally, the ratio of component (a) to component (b) preferably ranges from 1:99 to 99:1, more preferably from 1:30 to 30:1, and most preferably from 1:5 to 5:1.

The following weight ratios of TCMTB to the following organic acids are also preferred:

| TCMTB:sodium benzoic acid | 2:1 to 1:555 |
| TCMTB:sodium benzoate | 1:2.5 to 0.1:133 |
| TCMTB:p-hydroxybenzoic acid | 2:1 to 0.1:266 |
| TCMTB:sodium 2-hydroxybenzoate | 1:8 to 1:166 |
| TCMTB:dehydroacetic acid | 2:1 to 1:100 |
| TCMTB:sodium dehydroacetate | 1:5 to 1:67 |
| TCMTB:octanoic acid | 2:1 to 1:266 |
| TCXTB:nonanoic acid | 2:1 to 1:266 |
| TCMTB:formic acid | 1:2.5 to 1:133 |
| TCMTB:sorbic acid | 2:1 to 1:100 |
| TCMTB:potassium sorbate | 1:100 to 1:700 |
| TCMTB:acetic acid | 1:3 to 0.1:300 |
| TCMTB:oxalic acid | 2:1 to 1:166 |
| TCMTB:glycolic acid | 1:2.5 to 1:666 |
| TCMTB:citric acid | 1:5 to 1:166 |
| TCMTB:gluconic acid | 1:20 to 1:500 |
| TCMTB:malic acid | 1:2.5 to 1:666 |
| TCMTB:propionic acid | 1:1 to 0.1:133 |
| TCMTB:sodium propionate | 0.1:177 to 1:666 |
| TCMTB:lauric acid | 1:1 to 1:333 |
| TCMTB:undecylenic acid | 2:1 to 1:533 |
| TCMTB:sodium undecylenate | 1:20 to 0.1:100 |

Depending upon the specific application, the composition may be prepared in liquid form by dissolving the composition in an organic solvent. The preservative may be prepared in an emulsion form by emulsifying it in water, or if necessary, by adding a surfactant. Additional chemicals such as insecticides may be added to the foregoing preparation.

The synergistic activity of the combinations described above has been confirmed using standard laboratory techniques as illustrated below. The following examples are intended to illustrate, not limit, the present invention.

Microbiological Evaluation

A. Fungal Evaluation

Mineral salts-glucose medium was used. To prepare the medium, the following ingredients were added to 1 liter of deionized water: 0.7 g of $KH_2PO_4$, 0.7 g of $MgSO_4 \cdot 7H_2O$, 1.0 g of $NH_4NO_3$, 0.005 g NaCl, 0.002 g $FeSO_4 \cdot 7H_2O$, 0.002 g $ZnSO_4 \cdot 7H_2O$, 0.001 g $MnSO_4 \cdot 7H_2O$, 10 g of Glucose. The pH of the medium was adjusted to 6 with 1N NaOH. The medium was distributed in 50 g amounts in 250 mL flasks and autoclaved at 121° C. for 20 minutes. The fungus, *Trichoderma viride*, was grown on a potato dextrose agar slant for 7 to 10 days and a spore suspension prepared by washing down the spores from the slant into a sterile saline solution. After addition of the biocides in the desired concentrations to the sterile mineral salts-glucose medium, the fungal spore suspension was added. The final spore concentration was approximately $10^6$ cfu/mL. The inoculated media was incubated at 28° C. for 14 days.

B. Bacterial Evaluation

Nutrient broth (2.5 g/liter of deionized water) was prepared and the pH adjusted to 6 with 1N HCL. This was distributed in 5 mL amounts in test tubes and autoclaved for 20 minutes at 121° C. After addition of the biocides in the desired concentrations to the nutrient broth, 100 microliters of a suspension of *Pseudomonas aeruginosa* cells of approximately $9.3 \times 10^8$ cfc/mL were added and incubated at 37° C. for 48 hours.

In Examples 1 through 22, a synergistic effect was demonstrated in separate experiments by testing 2-(thiocyanomethylthio)benzothiazole, designated as component A and the corresponding organic acid or its salt as component B in a series of tests in varying ratios and a range of concentrations against the fungus, *Trichoderma viride* and also against the bacterium, *Pseudomonas aeruginosa* using the methods described above.

The lowest concentration of each mixture or compound which completely prevented growth of the fungi for two weeks and the bacteria for 48 hours was taken as the end points for synergism calculations. End points for the various mixtures were then compared with the end points for the pure active ingredients alone in concomitantly prepared flasks or test tubes.

Synergism was demonstrated by the method described by Kull, E. C., Eisman, P. C., Sylwestrwicz, H. D., and Mayer, R. L. 1961. Applied Microbiology. 9:538–541 wherein $QA/Qa + QB/Qb$ is less than 1

Qa=Concentration of compound A in parts per million, acting alone, which produced an end point.
Qb=Concentration of compound B in parts per million, acting alone, which produced an end point.
QA=Concentration of compound A in parts per million, in the mixture, which produced an end point.
QB=Concentration of compound B in parts per million, in the mixture, which produced an end point.

When the sum of QA/Qa and QB/Qb is greater than one, antagonism is indicated and when the sum is equal to one, additivity is indicated. When the sum of this value is less than one, synergism exists.

This procedure for demonstrating synergism of the compositions of this invention is a widely used and acceptable procedure. More detailed information is provided in the article by Kull et al. Further information concerning this procedure is contained in U.S. Pat. No. 3,231,509, which is incorporated herein by reference.

In general, however, an effective fungicidal and bactericidal response can be obtained when the synergistic combination is employed in concentrations ranging from about 0.1 to about 3000 ppm of 2-(thiocyanomethylthio)benzothiazole, preferably 0.1 to 1000 ppm, and most preferably 0.1 to 500 ppm, and from about 0.1 to about 1% of an organic acid, preferably 0.1 to 5000 ppm and most preferably 0.1 to 2000 ppm.

| Test organism | Quantities producing end points (ppm) | | | | | | |
|---|---|---|---|---|---|---|---|
| | $Q_a$ | $Q_A$ | $Q_b$ | $Q_B$ | $Q_A/Q_a$ | $Q_B/Q_b$ | $Q_A/Q_a + Q_B/Q_b$ |
| Example 1 Component A = TCMTB Component B = Benzoic acid | | | | | | | |
| Trichoderma viride | 9 | — | — | — | — | — | — |
| | — | 0.75 | — | 400 | 0.08 | 0.50 | 0.58 |
| | — | 1.5 | — | 200 | 0.17 | 0.25 | 0.42 |
| | — | 1.5 | — | 400 | 0.17 | 0.50 | 0.67 |
| | — | 3 | — | 25 | 0.33 | 0.03 | 0.36 |
| | — | 3 | — | 50 | 0.33 | 0.06 | 0.39 |
| | — | 3 | — | 100 | 0.33 | 0.13 | 0.46 |
| | — | 3 | — | 200 | 0.33 | 0.25 | 0.58 |
| | — | 3 | — | 400 | 0.33 | 0.50 | 0.83 |
| | — | — | 800 | — | — | — | — |
| Pseudomonas aeruginosa | 50 | — | — | — | — | — | — |
| | — | 1 | — | 100 | 0.02 | 0.4 | 0.42 |
| | — | 2.5 | — | 50 | 0.05 | 0.2 | 0.25 |
| | — | 2.5 | — | 100 | 0.05 | 0.4 | 0.45 |
| | — | 5 | — | 25 | 0.1 | 0.1 | 0.2 |
| | — | 5 | — | 50 | 0.1 | 0.2 | 0.3 |
| | — | 5 | — | 100 | 0.1 | 0.4 | 0.5 |
| | — | 10 | — | 5 | 0.2 | 0.02 | 0.22 |
| | — | 10 | — | 10 | 0.2 | 0.04 | 0.24 |
| | — | 10 | — | 25 | 0.2 | 0.1 | 0.3 |
| | — | 10 | — | 50 | 0.2 | 0.2 | 0.4 |
| | — | 10 | — | 100 | 0.2 | 0.4 | 0.6 |
| | — | — | 250 | — | — | — | — |
| Example 2 Component A = TCMTB Component B = Sodium benzoate | | | | | | | |
| Trichoderma viride | 9 | — | — | — | — | — | — |
| | — | 1.5 | — | 2000 | 0.17 | 0.67 | 0.84 |
| | — | 3 | — | 50 | 0.33 | 0.02 | 0.35 |
| | — | 3 | — | 100 | 0.33 | 0.03 | 0.36 |
| | — | 3 | — | 200 | 0.33 | 0.07 | 0.40 |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.67 | <1 |
| | — | — | >3000 | — | — | — | — |
| Pseudomonas aeruginosa | 50 | — | — | — | — | — | — |
| | — | 10 | — | 25 | 0.2 | 0.03 | 0.23 |
| | — | 10 | — | 50 | 0.2 | 0.05 | 0.25 |
| | — | 10 | — | 100 | 0.2 | 0.1 | 0.3 |
| | — | 10 | — | 250 | 0.2 | 0.25 | 0.45 |
| | — | 10 | — | 500 | 0.2 | 0.5 | 0.7 |
| | — | 10 | — | 1000 | 0.2 | 1 | 1.2 |
| | — | — | >1000 | — | — | — | — |
| Example 3 Component A = TCMTB Component B = p-hydroxybenzoic acid | | | | | | | |
| Trichoderma viride | 9 | — | — | — | — | — | — |
| | — | 0.75 | — | 2000 | 0.08 | 0.67 | 0.75 |
| | — | 1.5 | — | 1000 | 0.17 | 0.33 | 0.5 |
| | — | 1.5 | — | 2000 | 0.17 | 0.67 | 0.84 |
| | — | 3 | — | 25 | 0.33 | 0.00 | 0.33 |
| | — | 3 | — | 50 | 0.33 | 0.02 | 0.35 |
| | — | 3 | — | 100 | 0.33 | 0.03 | 0.36 |
| | — | 3 | — | 200 | 0.33 | 0.07 | 0.40 |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.67 | 1 |
| | — | — | 3000 | — | — | — | — |
| Pseudomonas aeruginosa | 50 | — | — | — | — | — | — |
| | — | 1.0 | — | 100 | 0.02 | 0.4 | 0.42 |
| | — | 2.5 | — | 100 | 0.05 | 0.4 | 0.45 |
| | — | 5 | — | 50 | 0.1 | 0.2 | 0.3 |
| | — | 5 | — | 100 | 0.1 | 0.4 | 0.5 |
| | — | 10 | — | 5 | 0.2 | 0.02 | 0.22 |
| | — | 10 | — | 10 | 0.2 | 0.04 | 0.24 |

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| | — | 10 | — | 25 | 0.2 | 0.1 | 0.3 |
| | — | 10 | — | 50 | 0.2 | 0.2 | 0.4 |
| | — | 10 | — | 100 | 0.2 | 0.4 | 0.6 |
| | — | — | 250 | — | — | — | — |

Example 4
Component A = TCMTB
Component B = 2-hydroxybenzoic acid (sodium salt)

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| *Trichoderma viride* | 9 | — | — | — | — | — | — |
| | — | 3 | — | 25 | 0.33 | 0.00 | 0.33 |
| | — | 3 | — | 50 | 0.33 | 0.02 | 0.35 |
| | — | 3 | — | 100 | 0.33 | 0.02 | 0.36 |
| | — | 3 | — | 200 | 0.33 | 0.07 | 0.40 |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.67 | <1.00 |
| | — | — | >3000 | — | — | — | — |
| *Pseudomonas aeruginosa* | 50 | — | — | — | — | — | — |
| | — | 10 | — | 250 | 0.2 | 0.25 | 0.45 |
| | — | 10 | — | 500 | 0.2 | 0.5 | 0.7 |
| | — | — | >1000 | — | — | — | — |

Example 5
Component A = TCMTB
Component B = Dehydroacetic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| *Trichoderma viride* | 9 | — | — | — | — | — | — |
| | — | 0.75 | — | 100 | 0.08 | 0.5 | 0.58 |
| | — | 1.5 | — | 100 | 0.17 | 0.5 | 0.67 |
| | — | 3.0 | — | 50 | 0.33 | 0.25 | 0.58 |
| | — | 3.0 | — | 100 | 0.33 | 0.5 | 0.83 |
| | — | 4.5 | — | 25 | 0.5 | 0.13 | 0.63 |
| | — | 4.5 | — | 50 | 0.5 | 0.25 | 0.75 |
| | — | 4.5 | — | 100 | 0.5 | 0.50 | 1 |
| | — | — | 200 | — | — | — | — |
| *Pseudomonas aeruginosa* | 50 | — | — | — | — | — | — |
| | — | 2.5 | — | 100 | 0.05 | 0.2 | 0.25 |
| | — | 2.5 | — | 250 | 0.05 | 0.5 | 0.55 |
| | — | 5 | — | 100 | 0.1 | 0.2 | 0.3 |
| | — | 5 | — | 250 | 0.1 | 0.5 | 0.6 |
| | — | 10 | — | 5 | 0.2 | 0.01 | 0.21 |
| | — | 10 | — | 10 | 0.2 | 0.02 | 0.22 |
| | — | 10 | — | 25 | 0.2 | 0.05 | 0.25 |
| | — | 10 | — | 50 | 0.2 | 0.1 | 0.3 |
| | — | 10 | — | 100 | 0.2 | 0.2 | 0.4 |
| | — | 10 | — | 250 | 0.2 | 0.5 | 0.7 |
| | — | — | 500 | — | — | — | — |

Example 6
Component A = TCMTB
Component B = Sodium dehydroacetate

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| *Trichoderma viride* | 9 | — | — | — | — | — | — |
| | — | 3 | — | 200 | 0.33 | 0.5 | 0.83 |
| | — | 4.5 | — | 25 | 0.5 | 0.06 | 0.56 |
| | — | 4.5 | — | 50 | 0.5 | 0.13 | 0.63 |
| | — | 4.5 | — | 100 | 0.5 | 0.25 | 0.75 |
| | — | 4.5 | — | 200 | 0.5 | 0.5 | 1 |
| | — | — | 400 | — | — | — | — |
| *Pseudomonas aeruginosa* | Combinations against *Pseudomonas aeruginosa* were not synergistic | | | | | | |

Example 7
Component A = TCMTB
Component B = Octanoic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| *Trichoderma viride* | 9 | — | — | — | — | — | — |
| | — | 1.5 | — | 400 | 0.17 | 0.5 | 0.67 |
| | — | 3 | — | 200 | 0.33 | 0.25 | 0.58 |
| | — | 3 | — | 400 | 0.33 | 0.50 | 0.83 |
| | — | 4.5 | — | 50 | 0.50 | 0.06 | 0.56 |
| | — | 4.5 | — | 100 | 0.50 | 0.13 | 0.63 |
| | — | 4.5 | — | 200 | 0.50 | 0.25 | 0.75 |
| | — | 4.5 | — | 400 | 0.50 | 0.50 | 1 |
| | — | — | 800 | — | — | — | — |
| *Pseudomonas aeruginosa* | 50 | — | — | — | — | — | — |
| | — | 1 | — | 250 | 0.02 | 0.5 | 0.52 |

-continued

| Test organism | Quantities producing end points (ppm) | | | | | | |
|---|---|---|---|---|---|---|---|
| | $Q_a$ | $Q_A$ | $Q_b$ | $Q_B$ | $Q_A/Q_a$ | $Q_B/Q_b$ | $Q_A/Q_a + Q_B/Q_b$ |
| | — | 2.5 | — | 100 | 0.05 | 0.2 | 0.25 |
| | — | 2.5 | — | 250 | 0.05 | 0.5 | 0.55 |
| | — | 5 | — | 100 | 0.1 | 0.2 | 0.3 |
| | — | 5 | — | 250 | 0.1 | 0.5 | 0.6 |
| | — | 10 | — | 5 | 0.2 | 0.01 | 0.21 |
| | — | 10 | — | 10 | 0.2 | 0.02 | 0.22 |
| | — | 10 | — | 25 | 0.2 | 0.05 | 0.25 |
| | — | 10 | — | 50 | 0.2 | 0.1 | 0.3 |
| | — | 10 | — | 100 | 0.2 | 0.2 | 0.4 |
| | — | 10 | — | 250 | 0.2 | 0.5 | 0.7 |
| | — | — | 500 | — | — | — | — |

Example 8
Component A = TCMTB
Component B = Nonanoic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 0.75 | — | 200 | 0.08 | 0.5 | 0.58 |
| | — | 1.5 | — | 200 | 0.17 | 0.5 | 0.67 |
| | — | 3 | — | 100 | 0.33 | 0.25 | 0.58 |
| | — | 3 | — | 200 | 0.33 | 0.5 | 0.83 |
| | — | 4.5 | — | 50 | 0.5 | 0.13 | 0.63 |
| | — | 4.5 | — | 100 | 0.5 | 0.25 | 0.75 |
| | — | 4.5 | — | 200 | 0.5 | 0.5 | 1.0 |
| | — | — | 400 | — | — | — | — |
| Pseudomonas aeruginosa | 50 | — | — | — | — | — | — |
| | — | 1 | — | 250 | 0.02 | 0.5 | 0.52 |
| | — | 2.5 | — | 100 | 0.05 | 0.2 | 0.25 |
| | — | 2.5 | — | 250 | 0.05 | 0.5 | 0.55 |
| | — | 5 | — | 100 | 0.1 | 0.2 | 0.3 |
| | — | 5 | — | 250 | 0.1 | 0.5 | 0.6 |
| | — | 10 | — | 5 | 0.2 | 0.01 | 0.21 |
| | — | 10 | — | 10 | 0.2 | 0.02 | 0.22 |
| | — | 10 | — | 25 | 0.2 | 0.05 | 0.25 |
| | — | 10 | — | 50 | 0.2 | 0.1 | 0.3 |
| | — | 10 | — | 100 | 0.2 | 0.2 | 0.4 |
| | — | 10 | — | 250 | 0.2 | 0.5 | 0.7 |
| | — | — | 500 | — | — | — | — |

Example 9
Component A = TCMTB
Component B = Formic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 800 | 0.33 | 0.16 | 0.49 |
| | — | 3 | — | 1000 | 0.33 | 0.20 | 0.53 |
| | — | 4.5 | — | 400 | .50 | 0.08 | 0.58 |
| | — | 4.5 | — | 800 | 0.50 | 0.16 | 0.66 |
| | — | 4.5 | — | 1000 | 0.50 | 0.20 | 0.70 |
| | — | — | >5000 | — | — | — | — |
| Pseudomonas aeruginosa | 50 | — | — | — | — | — | — |
| | — | 1 | — | 50 | 0.02 | 0.5 | 0.52 |
| | — | 2.5 | — | 50 | 0.05 | 0.5 | 0.55 |
| | — | 5 | — | 50 | 0.1 | 0.5 | 0.60 |
| | — | 10 | — | 25 | 0.2 | 0.25 | 0.45 |
| | — | 10 | — | 50 | 0.2 | 0.5 | 0.70 |
| | — | — | 100 | — | — | — | — |

Example 10
Component A = TCMTB
Component B = Sorbic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 100 | 0.33 | 0.5 | 0.83 |
| | — | 4.5 | — | 50 | 0.5 | 0.25 | 0.75 |
| | — | 4.5 | — | 100 | 0.5 | 0.50 | 1.0 |
| | — | — | 200 | — | — | — | — |
| Pseudomonas aeruginosa | 50 | — | — | — | — | — | — |
| | — | 1 | — | 100 | 0.02 | 0.4 | 0.42 |
| | — | 2.5 | — | 50 | 0.05 | 0.2 | 0.25 |
| | — | 2.5 | — | 100 | 0.05 | 0.4 | 0.45 |
| | — | 5 | — | 50 | 0.1 | 0.2 | 0.3 |
| | — | 5 | — | 100 | 0.1 | 0.4 | 0.5 |
| | — | 10 | — | 5 | 0.2 | 0.02 | 0.22 |
| | — | 10 | — | 10 | 0.2 | 0.04 | 0.24 |
| | — | 10 | — | 25 | 0.2 | 0.1 | 0.3 |
| | — | 10 | — | 50 | 0.2 | 0.2 | 0.4 |
| | — | 10 | — | 100 | 0.2 | 0.4 | 0.6 |

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| | — | — | 250 | — | — | — | — |

Example 11
Component A = TCMTB
Component B = Potassium sorbate

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 1.5 | — | 500 | 0.17 | 0.17 | 0.34 |
| | — | 3 | — | 500 | 0.33 | 0.17 | 0.50 |
| | — | 1.5 | — | 1000 | 0.17 | 0.33 | 0.50 |
| | — | 3 | — | 1000 | 0.33 | 0.33 | 0.66 |
| | — | 4.5 | — | 500 | 0.50 | 0.17 | 0.67 |
| | — | — | >3000 | — | — | — | — |
| Pseudomonas aeruginosa | Combinations against Pseudomonas aeruginosa were not synergistic | | | | | | |

Example 12
Component A = TCMTB
Component B = Acetic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 0.75 | — | 2000 | 0.08 | 0.67 | 0.75 |
| | — | 1.5 | — | 2000 | 0.17 | 0.67 | 0.84 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.67 | <1 |
| | — | 4.5 | — | 200 | 0.5 | 0.07 | 0.57 |
| | — | 4.5 | — | 400 | 0.5 | 0.13 | 0.63 |
| | — | 4.5 | — | 800 | 0.5 | 0.27 | 0.77 |
| | — | 4.5 | — | 1000 | 0.5 | 0.33 | 0.83 |
| | — | 4.5 | — | 2000 | 0.5 | 0.67 | 1.12 |
| | — | — | >3000 | — | — | — | — |
| Pseudomonas aeruginosa | 50 | — | — | — | — | — | — |
| | — | 2.5 | — | 50 | 0.05 | 0.5 | 0.55 |
| | — | 5 | — | 50 | 0.1 | 0.5 | 0.60 |
| | — | 10 | — | 25 | 0.2 | 0.25 | 0.45 |
| | — | 10 | — | 50 | 0.2 | 0.50 | 0.70 |
| | — | — | 100 | — | — | — | — |

Example 13
Component A = TCMTB
Component B = Oxalic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | <0.67 | <1 |
| | — | 4.5 | — | 100 | 0.5 | 0.03 | 0.53 |
| | — | 4.5 | — | 200 | 0.5 | 0.07 | 0.57 |
| | — | 4.5 | — | 400 | 0.5 | 0.13 | 0.63 |
| | — | 4.5 | — | 800 | 0.5 | 0.27 | 0.77 |
| | — | 4.5 | — | 1000 | 0.5 | 0.33 | 0.83 |
| | — | 4.5 | — | 2000 | 0.5 | 0.67 | 1.17 |
| | — | — | >3000 | — | — | — | — |
| Pseudomonas aeruginosa | 50 | — | — | — | — | — | — |
| | — | 1 | — | 100 | 0.02 | 0.4 | 0.42 |
| | — | 2.5 | — | 100 | 0.05 | 0.4 | 0.45 |
| | — | 5 | — | 100 | 0.1 | 0.4 | 0.5 |
| | — | 10 | — | 5 | 0.2 | 0.02 | 0.22 |
| | — | 10 | — | 10 | 0.2 | 0.04 | 0.24 |
| | — | 10 | — | 25 | 0.2 | 0.1 | 0.3 |
| | — | 10 | — | 50 | 0.2 | 0.2 | 0.4 |
| | — | 10 | — | 100 | 0.2 | 0.4 | 0.6 |
| | — | — | 250 | — | — | — | — |

Example 14
Component A = TCMTB
Component B = Glycolic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | <0.67 | <1.0 |
| | — | 4.5 | — | 25 | 0.5 | 0.00 | 0.50 |
| | — | 4.5 | — | 50 | 0.5 | 0.02 | 0.52 |
| | — | 4.5 | — | 100 | 0.5 | 0.03 | 0.53 |
| | — | 4.5 | — | 200 | 0.5 | 0.07 | 0.57 |

|  | Quantities producing end points (ppm) | | | | | | |
|---|---|---|---|---|---|---|---|
| Test organism | $Q_a$ | $Q_A$ | $Q_b$ | $Q_B$ | $Q_A/Q_a$ | $Q_B/Q_b$ | $Q_A/Q_a + Q_B/Q_b$ |
| | — | 4.5 | — | 400 | 0.5 | 0.13 | 0.63 |
| | — | 4.5 | — | 800 | 0.5 | 0.27 | 0.77 |
| | — | 4.5 | — | 1000 | 0.5 | 0.33 | 0.83 |
| | — | 4.5 | — | 2000 | 0.5 | 0.67 | 1.17 |
| | — | — | >3000 | — | — | — | — |
| Pseudomonas aeruginosa | 50 | — | — | — | — | — | — |
| | — | 2.5 | — | 100 | 0.05 | 0.4 | 0.45 |
| | — | 5 | — | 50 | 0.1 | 0.2 | 0.3 |
| | — | 5 | — | 100 | 0.1 | 0.4 | 0.5 |
| | — | 10 | — | 25 | 0.2 | 0.1 | 0.3 |
| | — | 10 | — | 50 | 0.2 | 0.2 | 0.4 |
| | — | 10 | — | 100 | 0.2 | 0.4 | 0.6 |
| | — | — | 250 | — | — | — | — |

Example 15
Component A = TCMTB
Component B = Citric acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 100 | 0.33 | 0.02 | 0.36 |
| | — | 3 | — | 200 | 0.33 | 0.07 | 0.40 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.67 | <1 |
| | — | 4.5 | — | 50 | 0.5 | 0.02 | 0.52 |
| | — | 4.5 | — | 100 | 0.5 | 0.03 | 0.53 |
| | — | 4.5 | — | 200 | 0.5 | 0.07 | 0.57 |
| | — | 4.5 | — | 400 | 0.5 | 0.13 | 0.63 |
| | — | 4.5 | — | 800 | 0.5 | 0.27 | 0.77 |
| | — | 4.5 | — | 1000 | 0.5 | 0.33 | 0.83 |
| | — | 4.5 | — | 2000 | 0.5 | 0.67 | 1.17 |
| | — | — | >3000 | — | — | — | — |
| Pseudomonas aeruginosa | 50 | — | — | — | — | — | — |
| | — | 10 | — | 50 | 0.2 | 0.2 | 0.4 |
| | — | 10 | — | 100 | 0.2 | 0.4 | 0.6 |
| | — | — | 250 | — | — | — | — |

Example 16
Component A = TCMTB
Component B = Gluconic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 4.5 | — | 100 | 0.5 | 0.07 | 0.57 |
| | — | 4.5 | — | 200 | 0.5 | 0.13 | 0.63 |
| | — | 4.5 | — | 400 | 0.5 | 0.27 | 0.77 |
| | — | 4.5 | — | 500 | 0.5 | 0.33 | 0.83 |
| | — | 4.5 | — | 1000 | 0.5 | 0.67 | 1.17 |
| | — | — | >1500 | — | — | — | — |
| Pseudomonas aeruginosa | 50 | — | — | — | — | — | — |
| | — | 1 | — | 500 | 0.02 | 0.5 | 0.52 |
| | — | 2.5 | — | 250 | 0.05 | 0.25 | 0.3 |
| | — | 2.5 | — | 500 | 0.05 | 0.5 | 0.55 |
| | — | 5 | — | 250 | 0.1 | 0.25 | 0.35 |
| | — | 5 | — | 500 | 0.1 | 0.5 | 0.6 |
| | — | 10 | — | 250 | 0.2 | 0.25 | 0.45 |
| | — | 10 | — | 500 | 0.2 | 0.5 | 0.7 |
| | — | — | 1000 | — | — | — | — |

Example 17
Component A = TCMTB
Component B = Malic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 3 | — | 200 | 0.33 | 0.07 | 0.40 |
| | — | 3 | — | 400 | 0.33 | 0.13 | 0.46 |
| | — | 3 | — | 800 | 0.33 | 0.27 | 0.60 |
| | — | 3 | — | 1000 | 0.33 | 0.33 | 0.66 |
| | — | 3 | — | 2000 | 0.33 | 0.56 | <1 |
| | — | 4.5 | — | 25 | 0.5 | 0.00 | 0.5 |
| | — | 4.5 | — | 50 | 0.5 | 0.02 | 0.52 |
| | — | 4.5 | — | 100 | 0.5 | 0.03 | 0.53 |
| | — | 4.5 | — | 200 | 0.5 | 0.07 | 0.57 |
| | — | 4.5 | — | 400 | 0.5 | 0.13 | 0.63 |
| | — | 4.5 | — | 800 | 0.5 | 0.27 | 0.77 |
| | — | 4.5 | — | 1000 | 0.5 | 0.33 | 0.83 |
| | — | 4.5 | — | 2000 | 0.5 | 0.67 | 1.17 |
| | — | — | >3000 | — | — | — | — |
| Pseudomonas | 50 | — | — | — | — | — | — |

|  | Quantities producing end points (ppm) | | | | | | |
|---|---|---|---|---|---|---|---|
| Test organism | $Q_a$ | $Q_A$ | $Q_b$ | $Q_B$ | $Q_A/Q_a$ | $Q_B/Q_b$ | $Q_A/Q_a + Q_B/Q_b$ |
| aeruginosa | — | 1 | — | 100 | 0.02 | 0.4 | 0.42 |
|  | — | 2.5 | — | 100 | 0.05 | 0.4 | 0.45 |
|  | — | 5 | — | 25 | 0.1 | 0.1 | 0.2 |
|  | — | 5 | — | 50 | 0.1 | 0.2 | 0.3 |
|  | — | 5 | — | 100 | 0.1 | 0.4 | 0.5 |
|  | — | 10 | — | 25 | 0.2 | 0.1 | 0.3 |
|  | — | 10 | — | 50 | 0.2 | 0.2 | 0.4 |
|  | — | 10 | — | 100 | 0.2 | 0.4 | 0.6 |
|  | — | — | 250 | — | — | — | — |

Example 18
Component A = TCMTB
Component B = Propionic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
|  | — | 0.75 | — | 800 | 0.08 | 0.4 | 0.48 |
|  | — | 0.75 | — | 1000 | 0.08 | 0.5 | 0.58 |
|  | — | 1.50 | — | 800 | 0.17 | 0.4 | 0.57 |
|  | — | 1.50 | — | 1000 | 0.17 | 0.5 | 0.67 |
|  | — | 3 | — | 400 | 0.33 | 0.20 | 0.53 |
|  | — | 3 | — | 800 | 0.33 | 0.4 | 0.73 |
|  | — | 3 | — | 1000 | 0.33 | 0.5 | 0.83 |
|  | — | — | 2000 | — | — | — | — |
| Pseudomonas aeruginosa | 50 | — | — | — | — | — | — |
|  | — | 25 | — | 25 | 0.5 | 0.1 | 0.6 |
|  | — | 25 | — | 50 | 0.5 | 0.2 | 0.7 |
|  | — | 25 | — | 100 | 0.5 | 0.4 | 0.9 |
|  | — | — | 250 | — | — | — | — |

Example 19
Component A = TCMTB
Component B = Sodium propionate

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
|  | — | 3 | — | 2000 | 0.33 | 0.67 | <1 |
|  | — | 4.5 | — | 800 | 0.5 | 0.27 | 0.77 |
|  | — | 4.5 | — | 1000 | 0.5 | 0.33 | 0.85 |
|  | — | 4.5 | — | 2000 | 0.5 | 0.67 | 1.12 |
|  | — | — | >3000 | — | — | — | — |
| Pseudomonas aeruginosa | Combinations against Pseudomonas aeruginosa were not synergistic. | | | | | | |

Example 20
Component A = TCMTB
Component B = Lauric acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
|  | — | 3 | — | 1000 | 0.33 | 0.5 | 0.83 |
|  | — | 4.5 | — | 400 | 0.5 | 0.2 | 0.70 |
|  | — | 4.5 | — | 800 | 0.5 | 0.4 | 0.90 |
|  | — | 3.4 | — | 1000 | 0.5 | 0.5 | 1.0 |
|  | — | — | 2000 | — | — | — | — |
| Pseudomonas aeruginosa | 50 | — | — | — | — | — | — |
|  | — | 25 | — | 25 | 0.5 | 0.03 | 0.53 |
|  | — | 25 | — | 50 | 0.5 | 0.05 | 0.55 |
|  | — | 25 | — | 100 | 0.5 | 0.1 | 0.6 |
|  | — | 25 | — | 250 | 0.5 | 0.25 | 0.75 |
|  | — | 25 | — | 500 | 0.5 | 0.5 | <1 |
|  | — | — | >1000 | — | — | — | — |

Example 21
Component A = TCMTB
Component B = Undecylenic acid

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
|  | — | 0.75 | — | 400 | 0.08 | 0.5 | 0.58 |
|  | — | 1.5 | — | 200 | 0.17 | 0.25 | 0.42 |
|  | — | 1.5 | — | 400 | 0.17 | 0.5 | 0.67 |
|  | — | 3.0 | — | 50 | 0.33 | 0.06 | 0.39 |
|  | — | 3.0 | — | 100 | 0.33 | 0.13 | 0.46 |
|  | — | 3.0 | — | 200 | 0.33 | 0.25 | 0.58 |
|  | — | 3.0 | — | 400 | 0.33 | 0.5 | 0.83 |
|  | — | 4.5 | — | 50 | 0.5 | 0.06 | 0.56 |
|  | — | 4.5 | — | 100 | 0.5 | 0.13 | 0.63 |
|  | — | — | 800 | — | — | — | — |
| Pseudomonas aeruginosa | 50 | — | — | — | — | — | — |
|  | — | 10 | — | 5 | 0.2 | 0.01 | 0.21 |
|  | — | 10 | — | 10 | 0.2 | 0.02 | 0.22 |
|  | — | 10 | — | 25 | 0.2 | 0.05 | 0.25 |

-continued

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| | — | 10 | — | 50 | 0.2 | 0.1 | 0.30 |
| | — | 10 | — | 100 | 0.2 | 0.2 | 0.4 |
| | — | 10 | — | 250 | 0.2 | 0.5 | 0.7 |
| | — | — | 500 | — | — | — | — |

Example 22
Component A = TCMTB
Component B = Sodium undecylenate

| Test organism | $Q_a$ | $Q_A$ | $Q_b$ | $Q_B$ | $Q_A/Q_a$ | $Q_B/Q_b$ | $Q_A/Q_a + Q_B/Q_b$ |
|---|---|---|---|---|---|---|---|
| Trichoderma viride | 9 | — | — | — | — | — | — |
| | — | 0.75 | — | 800 | 0.08 | 0.8 | 0.88 |
| | — | 1.5 | — | 400 | 0.17 | 0.4 | 0.57 |
| | — | 1.5 | — | 800 | 0.17 | 0.8 | 0.97 |
| | — | 3 | — | 400 | 0.33 | 0.4 | 0.73 |
| | — | 3 | — | 800 | 0.33 | 0.8 | 1.13 |
| | — | 4.5 | — | 100 | 0.5 | 0.1 | 0.6 |
| | — | 4.5 | — | 200 | 0.5 | 0.2 | 0.7 |
| | — | 4.5 | — | 400 | 0.5 | 0.4 | 0.9 |
| | — | 4.5 | — | 800 | 0.5 | 0.8 | 1.3 |
| | — | — | 1000 | — | — | — | — |
| Pseudomonas aeruginosa | 50 | — | — | — | — | — | — |
| | — | 25 | — | 500 | 0.5 | 0.5 | <1 |
| | — | — | >1000 | — | — | — | — |

What is claimed is:

1. A composition consisting essentially of (a) 2-(thiocyanomethylthio)benzothiazole and (b) at least one organic compound selected from the group consisting of benzoic acid, a salt thereof, p-hydroxybenzoic acid, a salt thereof, sodium benzoate, sodium 2-hydroxybenzoate, and mixtures thereof, wherein said components (a) and (b) are present in synergistic microbicidal effective amounts to control the growth of at least one microorganism selected from the group consisting of bacteria, fungi, and mixtures thereof.

2. The composition of claim 1, wherein said bacteria or fungi is Trichoderma viride or Pseudomonas aeruginosa.

3. The composition of claim 1, wherein the weight ratio of (a) to (b) is from about 1:99 to about 99:1.

4. The composition of claim 3, wherein the weight ratio of (a) to (b) is from about 1:30 to about 30:1.

5. The composition of claim 4, where the weight ratio of (a) to (b) is from about 1:5 to about 5:1.

6. The composition of claim 1, wherein said organic compound is benzoic acid or a salt thereof.

7. The composition of claim 1, wherein said organic compound is sodium benzoate.

8. The composition of claim 1, wherein said erganic compound is p-hydroxybenzoic acid or a salt thereof.

9. The composition of claim 1, wherein said organic compound is sodium 2-hydroxybenzoate.

10. A method of controlling the growth of at least one microorganism selected from the group consisting of bacteria and fungi in or on a material or medium susceptible to attack by the microorganism comprising the step of adding to the material or medium to control said growth a composition comprising synergistic microbicidal effective amounts of (a) 2-(thiocyanomethylthio)-benzothiazole and (b) at least one organic compound selected from the group consisting of benzoic acid, a salt thereof, p-hydroxybenzoic acid, a salt thereof sodium benzoate, sodium 2-hydroxybenzoate, and mixtures thereof.

11. The method of claim 10, wherein said bacteria or fungi is Trichoderma viride or Pseudomonas aeruginosa.

12. The method of claim 10, wherein said material or medium is wood pulp, wood chips, wood, lumber, paints, leathers, adhesives, coatings, animal hides, tanning liquors, paper mill liquors, metalworking fluids, starch, petrochemicals, acrylic latex paint emulsions, pharmaceutical formulations, cooling tower water, cosmetics and toiletry formulations, textiles, geological drilling lubricants or agrochemical compositions.

13. The method of claim 10, wherein the material or medium is in the form of a solid, dispersion, emulsion or solution.

14. The method of claim 10, wherein said components (a) and (b) can be added separately to the material or medium.

15. The method of claim 10, wherein said organic compound is benzoic acid or a salt thereof.

16. The method of claim 10, wherein said organic compound is sodium benzoate.

17. The method of claim 10, wherein said organic compound is p-hydroxybenzoic acid or a salt thereof.

18. The method of claim 10, wherein said organic compound is sodium 2-hydroxybenzoate.

19. A method for preventing spoilage of a material or medium caused by bacteria, fungi, or mixtures thereof comprising the step of adding to a material or medium to prevent spoilage a composition comprising synergistic microbicidal effective amounts of (a) 2-(thiocyanomethylthio)benzothiazole and (b) at least one organic compound selected from the group consisting of benzoic acid, a salt thereof, p-hydroxybenzoic acid, a salt thereof, sodium benzoate, sodium 2-hydroxybenzoate, and mixtures thereof.

20. The method of claim 19 wherein said material is seeds or crops.

21. The method of claim 19, wherein said organic compound is benzoic acid or a salt thereof.

22. The method of claim 19, wherein said organic compound is sodium benzoate.

23. The method of claim 19, wherein said organic compound is p-hydroxybenzoic acid or a salt thereof.

24. The method of claim 19, wherein said organic compound is sodium 2-hydroxybenzoate.

* * * * *

UNITED STATES PATENT AND TRADEMARK OFFICE
CERTIFICATE OF CORRECTION

PATENT NO.   : 5,494,904
DATED        : February 27, 1996
INVENTOR(S)  : D. Oppong et al.

It is certified that error appears in the above-identified patent and that said Letters Patent is hereby corrected as shown below:

Column 17, line 61 (claim 10), after "thereof", insert -- , --.

Signed and Sealed this

Thirteenth Day of August, 1996

Attest:

BRUCE LEHMAN

*Attesting Officer*   *Commissioner of Patents and Trademarks*